United States Patent
Rodrigues et al.

(10) Patent No.: US 10,126,254 B2
(45) Date of Patent: Nov. 13, 2018

(54) NON-UNIFORM PHOTON-COUNTING DETECTOR ARRAY ON A FOURTH-GENERATION RING TO ACHIEVE UNIFORM NOISE AND SPECTRAL PERFORMANCE IN Z-DIRECTION

(71) Applicant: Toshiba Medical Systems Corporation, Otawara (JP)

(72) Inventors: Miesher L Rodrigues, Buffalo Grove, IL (US); Hao Yang, Vernon Hills, IL (US); Liang Cai, Arlington Heights, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 455 days.

(21) Appl. No.: 14/575,783

(22) Filed: Dec. 18, 2014

(65) Prior Publication Data

US 2016/0178762 A1    Jun. 23, 2016

(51) Int. Cl.
*G01N 23/00* (2006.01)
*G01N 23/046* (2018.01)
(Continued)

(52) U.S. Cl.
CPC .......... *G01N 23/046* (2013.01); *A61B 6/032* (2013.01); *A61B 6/4233* (2013.01);
(Continued)

(58) Field of Classification Search
CPC ......... A61B 6/032; A61B 6/482; A61B 6/037; A61B 6/502; A61B 6/545; A61B 5/00; A61B 6/4233; A61B 6/54; A61B 6/4241; A61B 6/5205; A61B 6/4266; A61B 6/4258; A61B 5/0402; A61B 5/412; A61B 5/415; A61B 5/418; A61B 5/7264; A61B 5/7275; A61B 6/4291; A61B 6/4085; A61B 6/027; A61B 6/4028; A61B 6/463; A61B 6/4488; A61B 6/542; A61B 6/4014; A61B 6/4042;
(Continued)

(56) References Cited

U.S. PATENT DOCUMENTS

| | | | |
|---|---|---|---|
| 4,086,486 A * | 4/1978 | Bybee | G01T 1/2957 250/207 |
| 6,188,745 B1 * | 2/2001 | Gordon | A61B 6/032 378/15 |

(Continued)

FOREIGN PATENT DOCUMENTS

EP    1 120 666 A2    1/2001
WO   WO2010/073189 A1   7/2010

*Primary Examiner* — Irakli Kiknadze
(74) *Attorney, Agent, or Firm* — Oblon, McClelland, Maier & Neustadt, L.L.P.

(57) ABSTRACT

A computed tomography (CT) detector apparatus includes a plurality of detector arrays arranged in a ring, wherein for at least one array that includes a plurality of elements, an anode pixel pattern is non-uniform in a z-axis direction and a thickness of each element in the array is correspondingly non-uniform along the z-axis direction. A size of the anode pixels increases proportionally away from a center of the array, and a thickness of the elements increases away from the center of the array. The ratio of the thickness of the element to the size of the anode pixels is substantially the same over the array.

19 Claims, 7 Drawing Sheets

(51) Int. Cl.
*A61B 6/03* (2006.01)
*A61B 6/00* (2006.01)
*G01T 1/163* (2006.01)

(52) U.S. Cl.
CPC .......... *A61B 6/4241* (2013.01); *A61B 6/4266* (2013.01); *A61B 6/482* (2013.01); *G01T 1/1635* (2013.01)

(58) Field of Classification Search
CPC ......... A61B 6/06; A61B 6/4208; A61B 6/503; A61B 6/022; F01L 13/0005; F01L 2001/34433; F01L 2810/03; G01N 23/046; G01T 1/241; G01T 1/24; G01T 1/247; G01T 1/18; G01T 1/366; G01T 1/249; G01T 1/244; G01T 1/2928; G01T 1/2985; G01T 1/20; G01T 1/248; G01T 1/2935; G01T 1/2957; G01T 1/202; G01T 1/242; G01T 1/243; G01T 1/2018; G01T 1/1642; G01T 1/2006; G01T 1/208; G01T 1/245; H01L 27/14676; H01L 27/14696; H01L 31/022408; H01L 31/085; H01L 31/1828; H01L 27/14658
USPC .................... 378/4, 19, 20, 62; 250/580–591
See application file for complete search history.

(56) References Cited

U.S. PATENT DOCUMENTS

| | | | |
|---|---|---|---|
| 6,243,438 B1 * | 6/2001 | Nahaliel | A61B 6/032 378/19 |
| 6,535,571 B2 * | 3/2003 | Von Der Haar | A61B 6/032 250/370.09 |
| 6,792,068 B1 * | 9/2004 | Flohr | A61B 6/032 378/19 |
| 7,280,631 B2 * | 10/2007 | De Man | A61B 6/032 378/10 |
| 7,522,695 B2 * | 4/2009 | Nishide | A61B 6/032 250/370.09 |
| 7,697,659 B2 | 4/2010 | Hoffman et al. | |
| 7,705,319 B2 * | 4/2010 | Bale | G01T 1/24 250/338.4 |
| 7,916,836 B2 | 3/2011 | Tkaczyk et al. | |
| 9,018,589 B2 * | 4/2015 | Engel | G01T 1/24 250/370.01 |
| 9,119,589 B2 | 9/2015 | Zou | |
| 9,411,057 B2 * | 8/2016 | Helm | A61B 6/4208 |
| 2003/0085358 A1 * | 5/2003 | El-Hanany | G01T 1/241 250/370.13 |
| 2010/0213381 A1 | 8/2010 | Herrmann et al. | |
| 2011/0147600 A1 * | 6/2011 | Spahn | G01T 1/20 250/370.09 |
| 2013/0009067 A1 | 1/2013 | Schmand et al. | |
| 2013/0009267 A1 * | 1/2013 | Henseler | G01T 1/248 257/443 |
| 2013/0343517 A1 * | 12/2013 | Gagnon | G01T 1/24 378/19 |
| 2015/0085970 A1 * | 3/2015 | Bouhnik | A61B 6/4241 378/5 |
| 2015/0146844 A1 | 5/2015 | Zamyatin et al. | |
| 2015/0234058 A1 * | 8/2015 | Engel | G01T 1/241 250/370.08 |
| 2016/0089091 A1 * | 3/2016 | Gagnon | A61B 6/4241 378/5 |
| 2017/0059721 A1 * | 3/2017 | Simanovsky | G01T 1/2018 |

* cited by examiner

NON-UNIFORM PHOTON-COUNTING DETECTOR ARRAY ON A FOURTH-GENERATION RING TO ACHIEVE UNIFORM NOISE AND SPECTRAL PERFORMANCE IN Z-DIRECTION

FIELD

Embodiments disclosed herein generally relate to photon-counting detectors.

BACKGROUND

Traditional computed tomography (CT) scanners use energy-integrating detectors for acquiring energy integration X-ray data. An energy-integrating detector does not take advantage of the energy information in the X-ray beam. Even though the X-ray source emits X-rays in a broad spectrum, the detector is unable to differentiate between photons of different energy, but delivers an output signal proportional to the total energy of the photons registered during the readout interval. To obtain the spectral nature of the transmitted X-ray data, a photon-counting detector splits the X-ray beam into its component energies or spectrum bins and counts a number of photons in each of the bins. The use of the spectral nature of the X-ray source in CT is often referred to as spectral CT. Spectral CT imaging provides material separation capabilities that can potentially enable new clinical applications. The spectral images are usually presented as material concentration images of basis materials or mono-energetic images. For example, spectral CT is used in discriminating tissues, differentiating between materials such as tissues containing calcium and iodine, or enhancing the detection of smaller vessels. Among other advantages, spectral CT also reduces beam-hardening artifacts and increases accuracy in CT numbers independent of scanners.

Currently, most conventional designs acquire spectral information using either high- and low-energy X-ray sources or dual-detector-layer technologies. To improve the accuracy of material separation, photon-counting detector technologies can be used to provide good energy resolution. Photon-counting energy-resolved direct-conversion semiconductor detectors for computed tomography (CT) allow exploitation of the spectral information of each incident photon. X-ray photons interacting with the semiconductor sensors can be converted directly to electron-hole pairs without any inefficient intermediate processes, ensuring superior intrinsic energy resolution. However, for traditional multi-slice CT or cone-beam CT, the flux incident on each slice of a photon-counting detector is not uniform along the z-direction due to the different path lengths between the X-ray radiation source and each slice of the PCD.

BRIEF DESCRIPTION OF THE DRAWINGS

A more complete appreciation of the disclosed embodiments and the many attendant advantages thereof will be readily obtained as the same becomes better understood by reference to the following detailed description when considered in connection with the accompanying drawings, wherein.

DETAILED DESCRIPTION

In one embodiment, there is provided a computed tomography (CT) detector apparatus, the apparatus including a plurality of detector arrays arranged in a ring, wherein for at least one array including a plurality of elements, an anode pattern is non-uniform in a z-axis direction and a thickness of each element in the array is correspondingly non-uniform along the z-axis direction.

In one embodiment, the detector arrays are fixed photon-counting detector (PCD) arrays.

In accordance with an exemplary embodiment, while a detector apparatus to improve energy resolution at high count rate is described and discussed below with reference to a computed tomography (CT) imaging system, it should be understood that the method and system of the invention may be applied to other imaging systems using photon-counting detectors.

Figure 1:
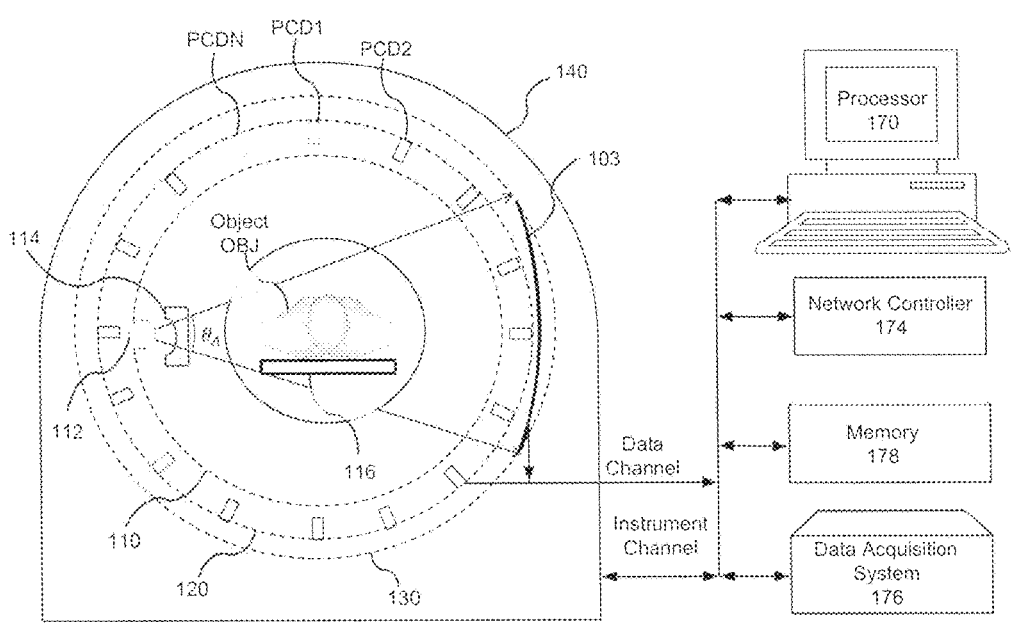
FIGS. 1 and 2 illustrate exemplary CT scanner systems.
Figure 2:
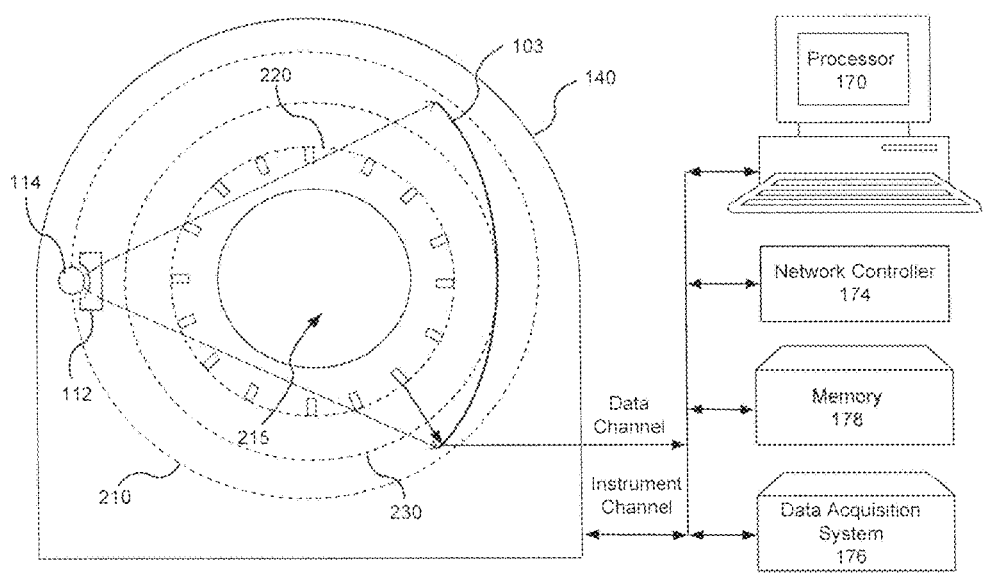

FIG. 1 and FIG. 2 show schematic views of CT scanner systems with hybrid systems having energy-integrating detectors arranged in a third-generation geometry and photon-counting detectors (PCDs) arranged in a fourth-generation geometry. FIG. 1 shows a coupled-ring topology with the X-ray source 114 inside the ring of PCDs and the X-ray detector unit 103 outside the ring of PCDs, as discussed in U.S. patent application Ser. No. 13/426,903, incorporated herein by reference in its entirety. In contrast, FIG. 2 shows an inner-ring topology with both the X-ray source 114 and the X-ray detector unit 103 outside the ring of PCDs, as discussed in U.S. patent application Ser. No. 14/092,998, incorporated herein by reference in its entirety.

Illustrated in FIG. 1 is an implementation for placing the PCDs in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector 103.

Also shown in FIG. 1 is circuitry and hardware for acquiring, storing, processing, and distributing X-ray projection data. The circuitry and hardware include: a processor 170, a network controller 174, a memory 178, and a data acquisition system 176.

In one implementation, the X-ray source 112 and the collimator/filter 114 are fixedly connected to a rotational component 110 that is rotatably connected to a gantry 140. The X-ray detector 103 is similarly fixedly connected to a rotational component 530 that is rotatably connected to the gantry 140. The PCDs are fixedly connected to a circular component 520 that is fixedly connected to the gantry 140. The gantry 140 houses many pieces of the CT scanner.

The gantry of the CT scanner also includes an open aperture 215 (shown in FIG. 2) enabling the object OBJ that is arranged on a table 216 positioned in a projection plane of the X-rays traveling from the X-ray source to the PCDs and detector unit 203. The "projection plane" is a volume wherein X-rays pass from the X-ray source 112 to the detectors including the PCDs and the detector unit 103. The "object space" is the intersection of the projection plane and the open aperture 215 of the gantry. The "image space" includes the union of projection planes corresponding to all projection angles of the X-ray source 112 as the X-ray source 112 rotates around the aperture of the gantry. The image space is generally larger than the object space enabling image reconstruction for a volume extending beyond the aperture of the gantry an into the structure of the gantry 140.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1 includes a detector unit 103 having energy-integrating detectors arranged in a conventional third-generation geometry. The detector elements in the detector unit 503 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow-tie filter), and the detector unit 503 rotate around the object OBJ while the photon-counting detectors PCD1 through PCDN are stationary with respect to the object OBJ. In one implementation, the X-ray source 512 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 is mounted at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the X-ray source 112 optionally travels a helical path relative to the object OBJ, wherein the table 116 moves the object OBJ linearly in a predetermined direction perpendicular to the rotational plane of the rotating portion 110 as the rotating portion 510 rotates the X-ray source 112 and detector unit 103 in the rotational plane.

The motion of the rotating portion 110 around the object OBJ is controlled by a motion control system. The motion control system can be integrated with a data acquisition system or can be separate providing one way information regarding the angular position of the rotating portion 510 and the linear position of the table 116. The motion control system can include position encoders and feedback to control the position of the rotating portion 110 and the table 116. The motion control system can be an open loop system, a closed loop system, or a combination of an open loop system and a closed loop system. The motion control system can use linear and rotary encoders to provide feedback related to the position of the rotating portion 110 and the position of the table 116. The motion control system can use actuators to drive the motion of the rotating portion 110 and the motion of the table 116. These positioners and actuators can include: stepper motors, DC motors, worm drives, belt drives, and other actuators known in the art.

The CT scanner also includes a data channel that routes projection measurement results from the photon counting detectors and the detector unit 103 to a data acquisition system 176, a processor 170, memory 178, network controller 174. The data acquisition system 176 controls the acquisition, digitization, and routing of projection data from the detectors. The data acquisition system 176 also includes radiography control circuitry to control the rotation of the annular rotating frames 110 and 130. In one implementation data acquisition system 176 will also control the movement of the bed 116, the operation of the X-ray source 112, and the operation of the X-ray detectors 103. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 170 and the data acquisition system 176 can make use of the memory 176 to store, e.g., projection data, reconstructed images, calibration data and parameters, and computer programs.

The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the CT scanner. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 2 illustrates an inner ring topology for a CT scanner. The primary difference between the CT scanner in FIG. 2 and the CT scanner in FIG. 2 is that in FIG. 2 the X-ray source 112 and the rotational component 210 to which the X-ray source 112 is fixed are outside the circular component 220 to which the PCDs are fixed.

In one implementation, the back surface of each PCD is provided a protective rear cover to shield the PCDs from irradiation from behind as the X-ray source 112 travels outside the first circular component 220 of the sparsely placed photon-counting detectors.

Both the X-ray source 112, collimator 114 (e.g., a bow-tie filter), and the detector unit 503 rotate around the object OBJ in aperture 215 while the photon-counting detectors PCD1 through PCDN are stationary with respect to the object OBJ in aperture 215. In one implementation, the X-ray source 112 and collimator 114 are mounted on the first rotation component 610 mounted in the gantry 140 so that the X-ray source 112 projects X-ray radiation with a predetermined source fan beam angle $\theta_A$ towards the object OBJ while the X-ray source 112 rotates around the object OBJ outside the sparsely placed photon-counting detectors PCD 1 through PCDN. Furthermore, the detector unit 103 having energy-integrating detectors arranged in a third-generation geometry is mounted on the second rotation component 630 that is rotatably fixed to the gantry 140. The detector unit 103 is maintained at a position diametrically opposed position from the X-ray source 112 with the object OBJ in the intermediary space between the X-ray source 112 and the detector unit 103—the rotation components 210 and 230 rotating outside the stationary circular component 220, on which the photon-counting detectors PCD1 through PCDN are fixed in a predetermined sparse arrangement.

Figure 3A:
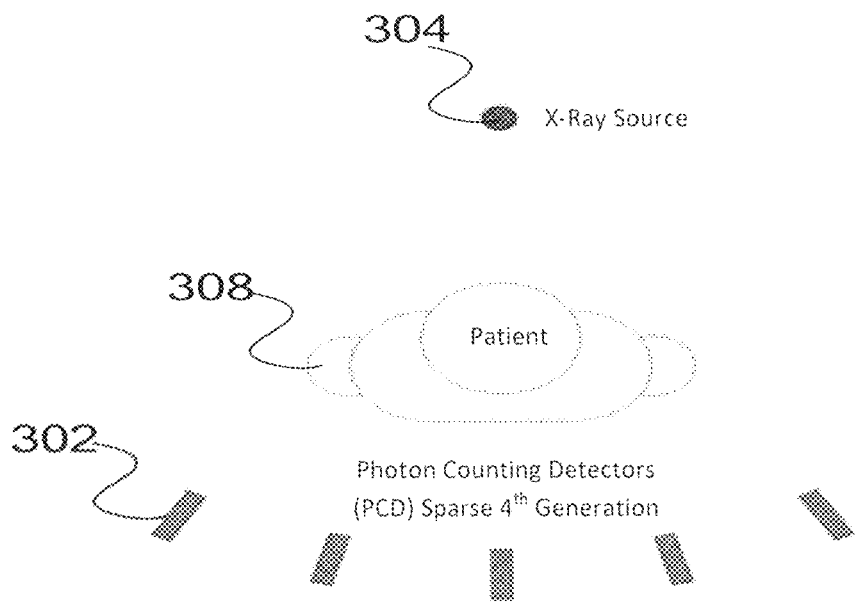
FIG. 3A illustrates an exemplary photon-counting detector array in a fourth-generation photon-counting CT scanner system.
Figure 3B:
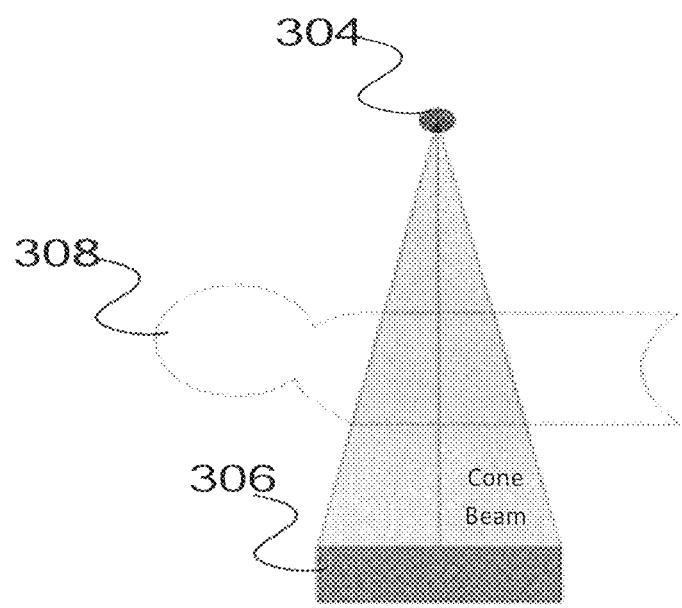
FIG. 3B illustrates an exemplary photon-counting detector array in a cone-beam CT scanner system.

As shown in FIG. 3A, for a fourth-generation photon-counting CT scanner with an X-ray radiation source 304, a predetermined number of the photon-counting detectors (PCDs) 302 are sparsely placed at fixed positions along a pre-determined circle around the object 308 to be scanned. FIG. 3B illustrates a cone-beam computed tomography (CBCT) scanner system with a photon-counting detector array (PCDA) 306. The PCDA 306 includes an array of PCDs 302. Each PCD 302 has a crystal formed from a semiconductor material, such as CdZnTe or CdTe. One face of the crystal has a large single-cathode electrode. The opposite face of the crystal is the anode side and includes an array of rectangular or square anode pixels of variable size.

In operation, a voltage difference is applied between the anode and the cathode so that a detector electrical field is generated. When a photon is incident on the crystal, the photon generally loses all energy within the crystal by ionization and leaves a pair of mobile electrons and holes in a small localized region of the crystal. As a result of the detector electric field, the holes drift to the cathode and the electrons drift to the anode. The resulting induced charges on the anode pixels are sensed and processed by appropriate electronic circuits. However, because distances between the X-ray source and each PCD 302 in the PCDA 306 are different, the flux incident on the fourth-generation direct-conversion PCDA 306 is not uniform in the axial direction (z-direction shown in FIG. 4).

Figure 4:
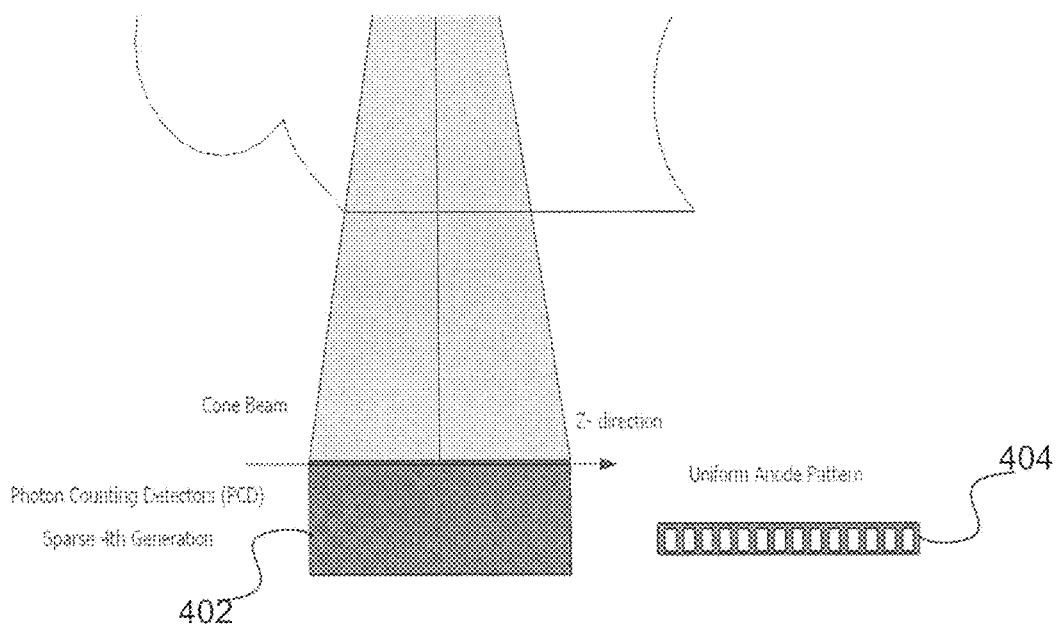
FIG. 4 illustrates an exemplary uniform anode pixel photon-counting detector array.

However, as most of the PCDAs 402 only have uniform-size anode pixels 404, as shown in FIG. 4, the flux incident at the central slice of the PCDA 402 is ~20% higher as compared to the flux incident at an edge slice on a multi-slice CT or cone-beam computed tomography system. The difference in flux is due to the longer path length to the edge slice compared to the path length to the central slice. Higher incident photon-flux near the central slice causes more-space charge build-up (e.g., polarization) at the central slice when using uniform PCDs 302. Therefore, the uniform PCDs 302 have the disadvantage of unbalanced noise in the z-direction.

Figure 5A:
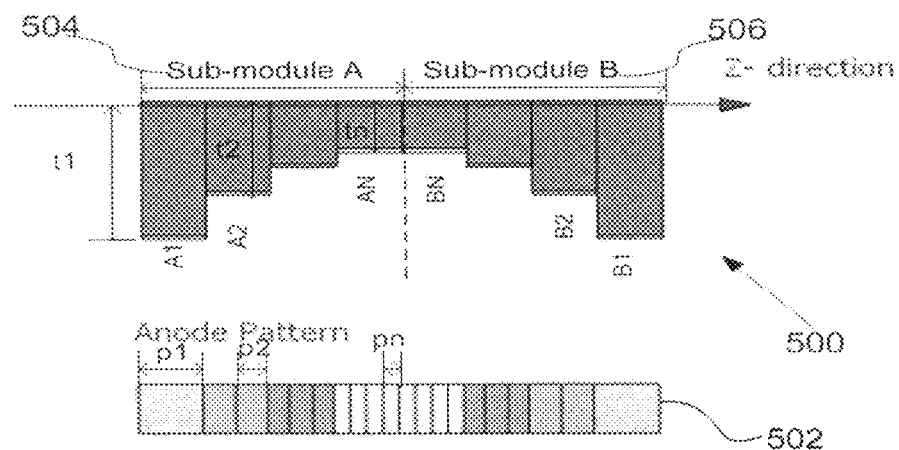
FIG. 5A illustrates an exemplary non-uniform detector array of PCDs with a uniform anode pixel pattern.

Now referring to FIG. 5A, one embodiment of a non-uniform PCDA 500 is illustrated. Compared with the uniform PCDA 402 shown in FIG. 4, the sizes of the anode pixels 502 are non-uniform in the z-direction and the thickness of the elements is correspondingly non-uniform along the z-direction. Thicker elements with larger pixel sizes are implemented closer to the edge of the extent of the cone beam in the axial (z) direction, and thinner elements with smaller pixel sizes are implemented closer to the center of the extent of the cone beam in the axial direction. The larger anode pixel sizes near the edge of the PCDA 500 compensate for the lower incident fluxes at the edge of the PCDA 500 and balance the noise. The thicker elements near the edges of the PCDA 500 compensate for the small-pixel effect, and thus preserve the energy resolution near the edges. Furthermore, the anode pixel sizes and the thickness of the elements are set so that the ratio of element thickness to anode size is substantially the same over the entire PCDA 500 along the z direction so as to balance noise and energy resolution in the z direction.

As shown in FIG. 5A, a PCDA 500 includes two symmetric sub-modules (a sub-module A 504 and a sub-module B 506), and each sub-module is symmetric to the other with respect to a central axis. For the sub-module A, which includes element A1 to AN, the anode pixel size and the thickness of A1 are p1 and t1, respectively, and the anode pixel size and the thickness of element AN are pn and tn, respectively. The ratio of the anode pixel size and the thickness of each element in sub-module A and B is such that:

$$\frac{p1}{t1} = \frac{pn}{tn} \quad (1)$$

In this particular embodiment, each element includes multiple pixels. For instance, several anode pixels of the same size are arranged in one element.

Figure 5B:
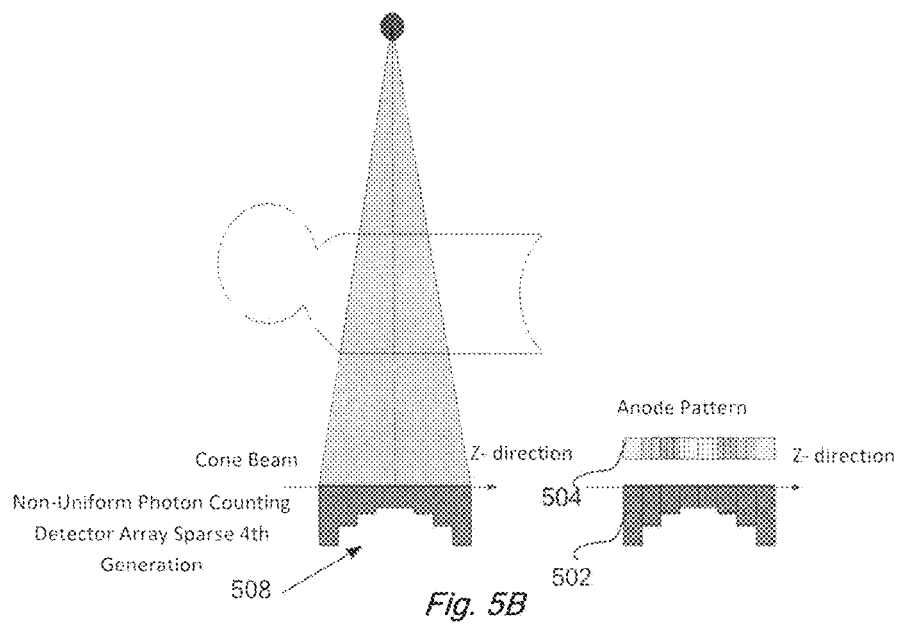
FIG. 5B illustrates an exemplary CT scanner system including a non-uniform detector array of PCDs with a uniform anode pixel pattern.

FIG. 5B illustrates an exemplary CT scanner system 508 including a non-uniform PCDA 502 with elements having uniform anode pixel patterns 504. Even though the flux incident at the central slice of the PCDA 502 is higher compared to the flux incident at the edge slice, the thicker elements with the larger anode pixel sizes near the edge of the PCDA 502 compensate for the lower incident fluxes at the edge of the PCDA 502, and therefore balance the noise. The thicker elements near the edge of the PCDA 502 also compensate for small-pixel effects and preserve the energy resolution near the edges.

Figure 6:
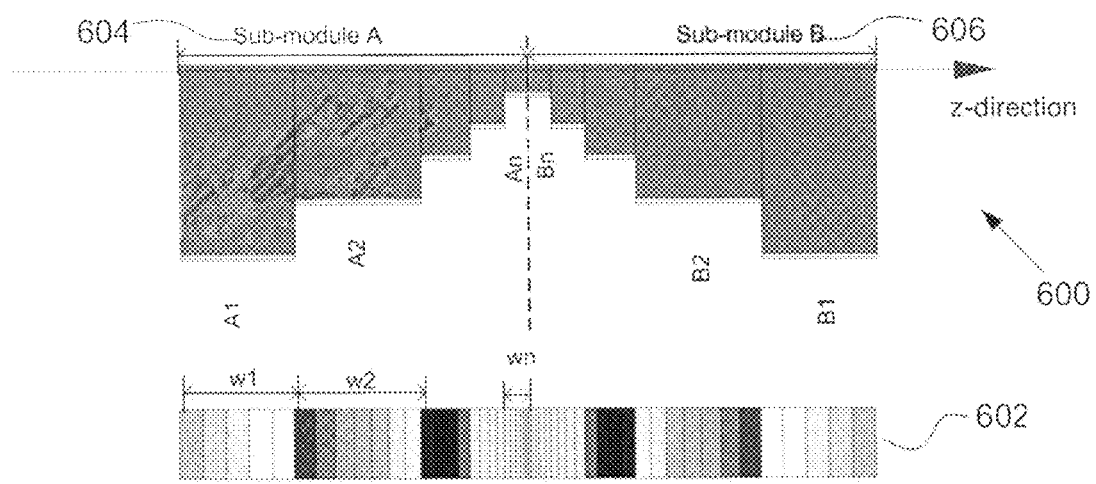
FIG. 6 illustrates an exemplary non-uniform detector array of PCDs with a non-uniform anode pixel pattern.

Now referring to FIG. 6, another embodiment of a non-uniform PCDA 600 is illustrated. The sizes of the anode pixel 602 are non-uniform in the z (axial) direction and the thicknesses of the elements are correspondingly non-uniform along the z direction. The thicker elements with larger pixel sizes are disposed closer to the edge, and the thinner elements with smaller pixel sizes are disposed closer to the center. Compared with the previous embodiment, each element has non-uniform pixels. Inside each element, the size of the anode pixels gradually increases towards the edge of the PCDA 600. Furthermore, the width of each element, gradually increases with the thickness of the respective element moving away from the center of the axis. For example, the width of element A1 (w1) is larger than the width of element AN (wn) in sub-module A 604. Otherwise, corresponding elements are similar to those described with respect to FIG. 5A.

Figure 7:
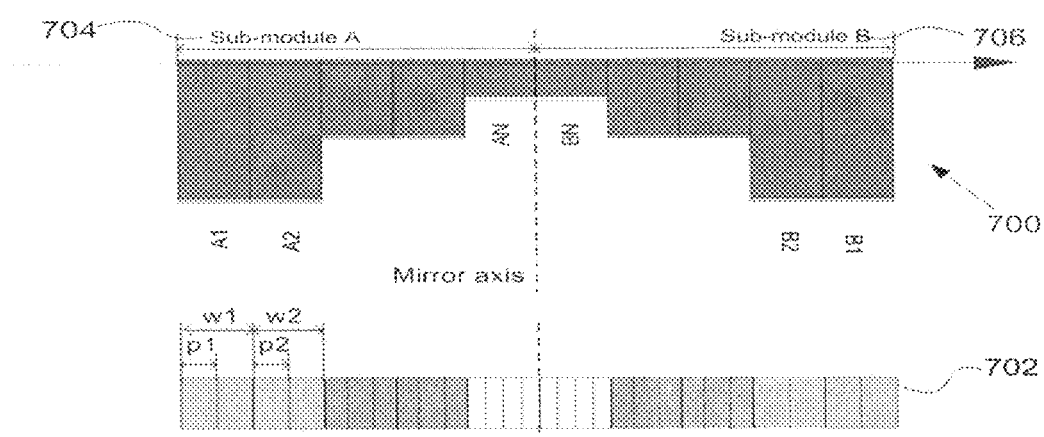
FIG. 7 illustrates an exemplary non-uniform detector array with multiple uniform PCDs.

Now referring to FIG. 7, another embodiment of a non-uniform PCDA 700 is illustrated. In this embodiment, the sizes of the anode pixels 702 are non-uniform in the z direction and the thickness of the element is correspondingly non-uniform along the z direction. Thicker elements with larger pixel sizes are disposed closer to the edge, and thinner elements with smaller pixel sizes are disposed closer to the center. Compared with the first embodiment, where each element has a different thickness and anode pixel pattern, several adjacent elements in the third embodiment have the same thickness, width, and a uniform anode pixel pattern. For example, as illustrated in FIG. 7, in sub-module A (704), the pixel size and the width for element A1 are p1 and w1, respectively, and the pixel size and the width of A2 are p2 and w2, where p1=p2 and w1=w2. Otherwise, corresponding elements are similar to those described with respect to FIG. 5A.

In all three embodiments, different detector thickness and anode pixels sizes are balanced in order to provide an equivalent small-pixel effect and to maintain optimal spectral performance in the z-direction.

The disclosed non-uniform PCDA configuration has the advantage of balancing noise in the z-direction. The space charge buildup (polarization) near the central slice of the PCDA is compensated for by implementing thinner elements near the center and thicker elements near the edge. The spectral performance (e.g., energy resolution) is equalized by maintaining an equivalent small-pixel effect throughout the entire PCDA.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:
1. A photon-counting detector (PCD), comprising:
a plurality of elements having an anode pixel pattern that is non-uniform in a first direction,
wherein a thickness of each element in an X-ray incident direction is correspondingly non-uniform along the first direction.

2. The apparatus of claim 1, wherein each element comprises:
a rectangular semiconductor crystal having a first face and a second face, wherein the first face and the second face are parallel;
a cathode side including a cathode electrode covering the first face; and
an anode side including a plurality of anode pixels on the second face.

3. The apparatus of claim 2, wherein a size of each anode pixel increases away from a center of the plurality of elements of the PCD in the first direction.

4. The apparatus of claim 3, wherein a thickness of each element increases away from the center of the plurality of elements of the PCD in the first direction.

5. The apparatus of claim 4, wherein the thickness of each element and the size of each anode pixel is balanced to provide an equivalent small-pixel effect and maintain an optimal spectral performance in the first direction.

6. The apparatus of claim 5, wherein a ratio of the thickness of each element to the size of each corresponding anode pixel is substantially a same over the plurality of elements of the PCD in the first direction.

7. The apparatus of claim 2, wherein the semiconductor crystal is one of CdZnTe and CdTe.

8. The apparatus of claim 1, wherein a size of each anode pixel corresponding an element is uniform.

9. The apparatus of claim 8, wherein two or more elements of the plurality of elements have a same thickness.

10. The apparatus of claim 1, wherein a size of each anode pixel corresponding to each element is non-uniform and increases proportionally away from a center of the plurality of elements of the PCD in the first direction.

11. A computed tomography (CT) imaging apparatus, comprising:
an X-ray source configured to emit X-rays to image an object; and
a photon-counting detector (PCD) configured to detect the emitted X-rays and including a plurality of elements having an anode pixel pattern that is non-uniform in a first direction,
wherein a thickness of each element in an incident direction of the X-rays is correspondingly non-uniform along the first direction.

12. The apparatus of claim 11, wherein each element comprises:
a rectangular semiconductor crystal having a first face and a second face, wherein the first face and the second face are parallel;
a cathode side including a cathode electrode covering the first face; and
an anode side including a plurality of anode pixels on the second face.

13. The apparatus of claim 12, wherein a size of each anode pixel increases away from a center of the plurality of elements of the PCD in the first direction.

14. The apparatus of claim 13, wherein a thickness of each element increases away from the center of the plurality of elements of the PCD in the first direction.

15. The apparatus of claim 14, wherein the thickness of each element and the size of each anode pixel is balanced to provide an equivalent small-pixel effect and maintain an optimal spectral performance in the first direction.

16. The apparatus of claim 15, wherein a ratio of the thickness of each element to the size of each corresponding anode pixel is substantially a same over the plurality of elements of the PCD in the first direction.

17. The apparatus of claim 11, wherein a size of each anode pixel corresponding an element is uniform.

18. The apparatus of claim 17, wherein two or more elements of the plurality of elements have a same thickness.

19. The apparatus of claim 11, wherein a size of each anode pixel corresponding to each element is non-uniform and increases proportionally away from a center of the plurality of elements of the PCD in the first direction.

* * * * *